(12) United States Patent
Cvetovich et al.

(10) Patent No.: US 6,489,507 B1
(45) Date of Patent: Dec. 3, 2002

(54) PROCESS FOR THE SYNTHESIS OF 3,5-BIS (TRIFLUOROMETHYL)BENZOIC ACID

(75) Inventors: Raymond Cvetovich, Scotch Plains, NJ (US); John Leazer, Metuchen, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/590,427

(22) Filed: Jun. 8, 2000

Related U.S. Application Data

(60) Provisional application No. 60/138,719, filed on Jun. 11, 1999.

(51) Int. Cl.[7] .......................... C07C 63/00; C07C 63/04
(52) U.S. Cl. ....................................... 562/405; 562/493
(58) Field of Search .................................. 562/405, 493

(56) References Cited

U.S. PATENT DOCUMENTS 5,910,605 A * 6/1999 Cosmo et al.

FOREIGN PATENT DOCUMENTS

GB 1028599 * 9/1964

OTHER PUBLICATIONS

Lichtenberger et al, Bull. Chem. Soc. 587, 1962.*
Aldrich, Handbook of Fine Chemicals, 2000, pp. 219–220.*
Porwisiak et al Chem. Ber. 1996, pp. 233–235.*
Lichtenberger et al Bull. Chem. Soc. pp. 587, 1962.*

* cited by examiner

*Primary Examiner*—Alan L. Rotman
*Assistant Examiner*—Héctor M Reyes
(74) *Attorney, Agent, or Firm*—J. Eric Thies; Melvin Winokur

(57) ABSTRACT

The present invention is concerned with a novel process for the preparation of 3,5-bis(trifluoromethyl)benzoic acid (CAS 725-89-3). This compound is useful as an intermediate in the synthesis of compounds which possess pharmacological activity, in particular, as substance P (neurokinin-1) receptor antagonists.

10 Claims, No Drawings

PROCESS FOR THE SYNTHESIS OF 3,5-BIS(TRIFLUOROMETHYL)BENZOIC ACID

This application claims benefit of Provisional Application Ser. No. 60/138,719 filed Jun. 11, 1999.

BACKGROUND OF THE INVENTION

The present invention relates to processes for the preparation of 3,5-bis(trifluoromethyl)benzoic acid (CAS 725-89-3) which is useful as an intermediate in the preparation of certain therapeutic agents. In particular, the present invention provides a process for the preparation of 3,5-bis(trifluoromethyl)benzoic acid which is an intermediate in the synthesis of pharmaceutical compounds which are substance P (neurokinin-1) receptor antagonists.

The preparation of 3,5-bis(trifluoromethyl)benzoic acid from 3,5-bis(tiifluoromethyl)bromobenzene has been reported by Lichtenberger, J.; Weiss, F. *Bull. Chem. Soc. Fr.*, 587, (1962). However, this reference quotes only a 49.5% yield of 3,5-bis(trifluoromethyl)benzoic acid from 3,5-bis(tifluoromethyl)bromobenzene.

The general processes disclosed in the art for the preparation of 3,5-bis(trifluoromethyl)benzoic acid result in relatively low and inconsistent yields of the desired product. In contrast to the previously known processes, the present invention provides effective methodology for the preparation of 3,5-bis(trifluoromethyl)benzoic acid in relatively high yield.

It will be appreciated that 3,5-bis(tiifluoromethyl)benzoic acid is an important intermediate for a particularly useful class of therapeutic agents. As such, there is a need for the development of a process for the preparation of 3,5-bis(trifluoromethyl)benzoic acid which is readily amenable to scale-up, uses cost-effective and readily available reagents and which is therefore capable of practical application to large scale manufacture.

Accordingly, the subject invention provides a process for the preparation of 3,5-bis(trifluoromethyl)benzoic acid via a very simple, short and highly efficient synthesis.

SUMMARY OF THE INVENTION

The novel process of this invention involves the synthesis of 3,5-bis(trifluoromethyl)benzoic acid. In particular, the present invention is concerned with novel processes for the preparation of a compound of the formula:

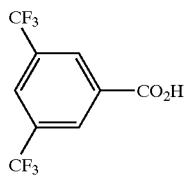

This compound is an intermediate in the synthesis of compounds which possess pharmacological activity. In particular, such compounds are substance P (neurokinin-1) receptor antagonists which are useful e.g., in the treatment of inflammatory diseases, psychiatric disorders, and emesis.

DETAILED DESCRIPTION OF THE INVENTION

The present invention is directed to processes for the preparation of 3,5-bis(trifluoromethyl)benzoic acid of the formula:

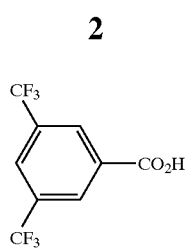

A preferred embodiment of the general process for the preparation of 3,5-bis(trifluoromethyl)-benzoic acid is as follows:

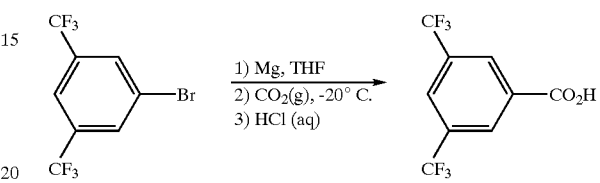

In accordance with the present invention, the treatment of the Grignard reagent from 3,5-bis(trifluoromethyl)bromobenzene with carbon dioxide gas at a temperature of less than about 0° C. and preferably less than about −20° C. provides 3,5-bis(trifluoromethyl)benzoic acid in higher yields than the processes disclosed in the art.

In a preferred embodiment, Grignard carboxylation of 3,5-bis-(trifluoromethyl)bromobenzene with $Mg/CO_2$ in tetrahydrofuran, followed by crystallization of the product gives 3,5-bis(trifluoromethyl)benzoic acid.

In a preferred embodiment, the present invention is directed to a process for the preparation of 3,5-bis(trifluoromethyl)benzoic acid which comprises the reaction of 3,5-bis(trifluoromethyl)bromobenzene with magnesium in tetrahydrofuran to form a Grignard reagent followed by addition of the addition of carbon dioxide gas to the solution of the Grignard reagent in tetrahydrofuran and treatment with a strong acid to give 3,5-bis(trifluoromethyl)benzoic acid.

A specific embodiment of the present invention concerns a process for the preparation of 3,5-bis(trifluoromethyl)benzoic acid of the formula:

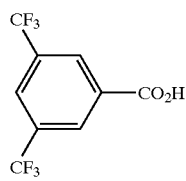

which comprises:

treating 3,5-bis(trifluoromethyl)benzene of the formula:

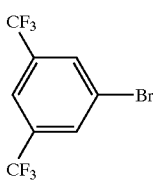

with magnesium in an organic solvent to form the Grignard reagent of the formula:

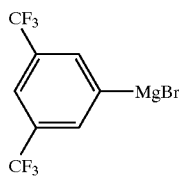

b) followed by treating the Grignard reagent with carbon dioxide gas in an organic solvent at an initial temperature of less than about 0° C., c) followed by treatment of the product therefrom with a strong acid to give 3,5-bis(trifluoromethyl)benzoic acid of the formula:

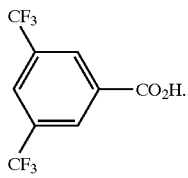

Preferred organic solvents for conducting the instant process include toluene, tetrahydrofuran (THF), diethyl ether, diglyme, methyl t-butyl ether. The more preferred organic solvent is tetrahydrofuran. In the formation of the Grignard reagent, tetrahydrofuran or diethyl ether are the more preferred organic solvents and tetrahydrofuran is the most preferred organic solvent.

The magnesium employed to prepare the Grignard reagent may be in the form of magnesium granules, magnesium turnings, magnesium dust, magnesium powder, suspension of magnesium in oil, and the like. To minimize safety risks, the use of magnesium granules is preferred.

In the present invention, it is preferred that the carbon dioxide be employed as carbon dioxide gas. It is more preferred that the carbon dioxide gas be at a pressure of 1 to 40 psi, it is still more preferred that the carbon dioxide gas be at a pressure of about 2 to 10 psi and it is even more preferred that the carbon dioxide gas be at a pressure of about 3 psi.

In the reaction of the Grignard reagent with carbon dioxide, it is preferred that the temperature upon addition of the carbon dioxide be less than about 0° C. It is further preferred that the temperature of the reaction mixture upon addition of the carbon dioxide is less than about –10° C. In the reaction of the Grignard reagent with carbon dioxide, it is more preferred that the temperature upon addition of the carbon dioxide be less than about –20° C., it is even more preferred that the temperature upon addition of the carbon dioxide be less than about –40° C., and it is still more preferred that the temperature upon addition of the carbon dioxide be less than about –45° C.

In the present invention, it is preferred that the carbon dioxide be present in solution in the solvent at a concentration which provides optimal reaction with the Grignard reagent. The concentration of the carbon dioxide in the solvent may be enhanced by increasing the pressure of the carbon dioxide gas and/or decreasing the temperature of the solution.

Preferred strong acids for use in the instant process include hydrochloric acid, sulfuric acid, methanesulfonic acid, and the like. A more preferred strong acid for use in the present invention is hydrochloric acid.

Grignard formation from 3,5-bis(trifluoromethyl) bromobenzene under typical conditions using magnesium turnings (4 equiv.) labeled as "suitable for Grignard reactions", diethyl ether solvent, and slow addition of the starting bromide resulted in facile formation of Grignard adduct (1–2 hours).

The use of less than 2.1 eq of magnesium turnings resulted in incomplete consumption of bromide (residual bromide>2–3 A%), while the use of more than 2.1 eq of magnesium turnings offered no advantage. A comparison of magnesium dust (freshly prepared), powder (50 mesh) and granules (20 mesh) showed that the Grignard reaction was complete for all within 1–2 hours at reflux in THF. The use of one type of magnesium over another (except for turnings) offered no advantage in terms of reaction profile, purity, or yield of the desired product. The use of magnesium granules is preferred, however, because magnesium granules present less of a safety hazard.

The Grignard formation is typically performed in tetrahydrofuran at reflux. The reaction is exothermic and the reaction may be controlled by the rate of addition of the bromide to the magnesium slurry. The reaction mixture is generally aged at reflux until <1 mol % of bromide remains. Grignard formation is usually complete within 2 hours, however reaction times of up to 5 hours give comparable yields of 3,5-bis(trifluoromethyl)benzoic acid.

A solution of the Grignard reagent is then transferred to a pressure bottle where it is treated with a constant pressure of $CO_2$. The carboxylation step was initially run at 20–25 psi for 3 hours at ambient temperature. In these preliminary investigations 3,5-bis(trifluoromethyl)benzoic acid was typically isolated acid in 76–78% yield ($\geq$98 wt %). At lower pressure (3 psi and ambient temperature), the assay yield of acid is less than those reactions run at 20–25 psi. The reaction profiles at 20–25 psi and 200 psi (ambient temperature) are essentially the same, thus higher pressure is generally unnecessary. At 20–25 psi, a moderate exotherm is observed upon introduction of the $CO_{2(gas)}$, as the reaction temperature increases from 0° C. to 15° C. over ~3–4 minutes. At 200 psi the reaction exotherms from 0° C. to 27° C. instantaneously. A similar exotherm (–40° C. to –25° C.) is observed at –40° C. addition of $CO_{2(gas)}$ at 20–25 psi. This suggests that exotherm control has minimal impact on reaction yield. The more important factor is the temperature of the reaction mixture as the $CO_{2(gas)}$ is first introduced. The carboxylation reaction is generally complete within one hour and the reaction profile remains essentially unchanged between one hour and 17 hours.

In accordance with the present invention, when the carboxylation was performed at –40° C. the production of the proteo byproduct tris[3,5-bis(trifluoromethyl)benzene was minimized to 5% with a resulting 5% increase in carboxylation 3,5-bis(trifluoromethyl)benzoic acid. The proteo level rose back to the 10–11% level when the reaction is run at 0° C. or –20° C. Moreover, at –40° C., the $CO_2$ pressure could be decreased to 2 psi with no ill effects, presumably due to an increase in $CO_2$ solubility at lower temperatures.

In the present invention, it is preferred that the $CO_2$ be added to a solution of the Grignard in THF at –40° C. When the Grignard was added to a $CO_2$ saturated THF solution at –40° C. an increase in the production of the proteo byproduct was observed. In addition, it is preferred that the pressure of $CO_2$ be greater than atmospheric pressure. When the Grignard was prepared under a static atmosphere of $CO_2$ (atmospheric pressure) significant byproduct formation was observed.

The acid is dissolved into aqueous base, and the neutral components are removed by extraction. 5% Aqueous NaOH, 5% aqueous $Na_2CO_3$ and 5% aqueous $K_2CO_3$ were evaluated as potential bases. 5% Na$_2$CO$_3$ was deemed the base of choice as this reagent did not lead to formation of as much of an emulsion as the other bases. Toluene, MTBE, EtOAc, and IPAc may be employed as wash solvents, however, EtOAc and IPAc are not preferred due to concerns over acetate hydrolysis, and MTBE and IPAc are not preferred due to high sodium salt solubility in these solvents. Toluene is the preferred extraction solvent. If, after quench and workup, the aqueous layer contains more than 2 mole % product, the aqueous layer may be backextracted with toluene to recover additional product.

In a preferred embodiment, the sodium salt is filtered through a bed of filter aid (such as solka floc) to ensure crystallization of the acid upon acidification. Attempted crystallization of the acid, without filtration of sodium salt, results in the acid oiling out of solution because the residue which is filtered off contains a small amount of dimer, some acid, and other unidentified byproducts. The oil may be converted to crystalline material by adding excess acid (conc. HCl) and aging overnight. Acid obtained by conversion of the oil is typically 80–90 wt %. By following a preferred embodiment of the present invention by utilizing filter aid filtration however, a 94% yield of material that is 99 wt % is typically isolated as a highly crystalline solid.

The 3,5-bis(trifluoromethyl)benzoic acid obtained in accordance with the present invention may be used as starting material in further reactions directly or following crystallization.

Many of the starting materials are either commercially available or known in the literature and others can be prepared following literature methods described for analogous compounds. The skills required in carrying out the reaction and purification of the resulting reaction products are known to those in the art. Purification procedures include crystallization, normal phase or reverse phase chromatography.

The following examples are provided for the purpose of further illustration only and are not intended to be limitations on the disclosed invention.

EXAMPLE 1

3,5-Bis(trifluoromethyl)bromobenzene

CF$_3$-C$_6$H$_3$-CF$_3$ →(Sulfuric Acid, Acetic Acid, DBH)→ CF$_3$-C$_6$H$_2$(Br)-CF$_3$

| Materials | MW | Density | Amount | Mmol | Equiv. |
|---|---|---|---|---|---|
| 1,3-Bis(trifluoromethyl)benzene | 214.1 | 1.38 | 107 g | 500 | 1.0 |
| 96% H$_2$SO$_4$ | | | 142 mL | | |
| Glacial HOAc | | | 22 mL | | |
| 1,3-Dibromo-5,5-dimethylhydantoin | 285.93 | | 77.25 g | 270 | 1.08 (Br$^+$) |
| 5N Aq NaOH | | | 75 mL | | |

To glacial acetic acid (22.0 mL), cooled to 15° C. in a 1 L 3-n RB flask (equipped with mechanical stirrer, thermocouple, and addition funnel), was added concentrated (96%) sulfuric acid (142 mL) in one portion. An exothermic heat of solution raised the temperature to 35° C. After cooling to 25° C., 1,3-bis(trifluoromethyl)benzene (107 g, 500 mmol) was added. With the acid mixture rapidly stirring, 1,3-dibromo-5,5-dimethylhydantoin (77.25 g; 270 mmol) was added over 2 min to give a multiple phase mixture (solid and two liquid). An exothermic reaction occurred that raised the internal temperature to ~40° C. (jacket cooling at 15° C.). After the reaction temperature began to drop (after 5 min) the reaction mixture was maintained at 45° C. for 4.5 hr.

The rate and selectivity of the bromination is highly dependent on the agitation of the two phase reaction. Slower stirring increases the amount of bis-bromination and slows the overall rate of reaction. The reaction mixture remains heterogeneous throughout the reaction and the organic phase separates when agitation is interrupted. At the end of the reaction, the phases separate slowly (bromide density= 1.699). The rate of bromination is also dependent on the ratio of acetic to sulfuric acid.

Progress of the reaction is monitored by GC analysis, as follows. Sample: ~50 µl of mixed phase, dilute with cyclohexane (1.5 mL), wash with water (1 mL), then 2N NaOH (1 mL), separate and inject. Resteck RTX-1701 [60 meter× 0.320 mm]: 100° C.; ramp: 5° C./min to 200° C.; 200° C. for 10 min; Flow 1.15 mL/min R$_t$:1,3-bis(trifluoromethyl)benzene: 7.0 min
3,5-bis(trifluoromethyl)bromobenzene: 9.4 min
Biaryl: 19.2 min The mixture was cooled to 2° C. and poured slowly into cold water (250 mL). The mixture was stirred vigorously for 10 min, allowed to settle, and the lower organic layer was separated and washed with 5N NaOH (75 mL) to give 145.1 g of a clear, colorless organic layer.

The assay yield of 1,3-bis(trifluoromethyl)bromobenzene was 93.7% (137.3 g, 469 mmol), which contained 0.6% 1,3-bis(trifluoromethyl)benzene, 1.0% 1,2-dibromo-3,5-bis(trifluoromethyl)benzene, and 0.3% 1,4-dibromo-3,5-bis-(trifluoromethyl)benzene. Total isomer byproducts measured by GC were 2.0 mol %.

EXAMPLE 2

3,5-Bis(trifluoromethyl)benzoic acid

CF$_3$-C$_6$H$_2$(CF$_3$)-Br →(1) Mg, THF; 2) CO$_2$(g), -20° C.; 3) HCl (aq))→ CF$_3$-C$_6$H$_2$(CF$_3$)-CO$_2$H

| Materials | MW | Density | Amount | Mmol | Equiv |
|---|---|---|---|---|---|
| 3,5-Bis-(trifluoromethyl)-bromobenzene, 94.4 wt % | 293.03 | 1.699 g/L | 31.05 g | 100 | 1.00 |
| Magnesium granules, 20 mesh | | | 5.10 g | | 2.1 |
| THF (KF = 60 µg/mL) | | | 300 mL | | |
| Toluene | | | 675 mL | | |
| Water | | | 200 mL | | |
| 5% Na$_2$CO$_3$ | | | 200 mL | | |
| 2N HCl | | | 200 mL | | |
| Solka Floc | | | 14 g | | |
| Conc. HCl | | | 40 mL | | |

To a 500 mL 3-neck round bottom flask equipped with an addition funnel, N$_2$ inlet, and a Teflon coated thermocouple was added magnesium granules (5.10 g, 210 mmol) and THF (200 mL). The mixture was heated to reflux. 3,5-Bis(trifluoromethyl)bromobenzene (31.05 g, 100 mmol) was dissolved in 50 mL of THF. The bromide solution (5 mL) was then added to the gently refluxing magnesium slurry over 2 minutes to initiate the Grignard reaction. After Grignard initiation, the remaining bromide was added over ½ hour.

An initial induction period of 5 minutes is generally allowed for. If the reaction does not initiate, another 5% charge of bromide solution is added. If the reaction still does not initiate after a bromide charge of 10%, 100 mg of iodine is added. The reaction exotherm was controlled by slowing or stopping the bromide addition if the reaction appeared too violent.

After complete bromide addition (~30 minutes), the dark brown solution was heated at gentle reflux for an additional 30 minutes. The reaction was monitored by HPLC (sample preparation: 100 μL sample quenched into 3.5 mL of 1:1 THF:2N HCl, then diluted to 100 mL in 65:35 acetonitrile:pH 6 buffer). Grignard formation was considered complete when the bromide level is less that 1 mol %.

After cooling to ambient temperature in a water bath, the mixture was transferred via cannula to an 800 mL pressure bottle equipped with a Teflon coated thermocouple and a vacuum/$N_2$/$CO_2$ inlet. THF (50 mL) was used as rinse. The contents of the pressure bottle were cooled to −45° C. under a $N_2$ atmosphere and briefly degassed in vacuo. The vessel was then pressurized at −45° C. to 3 psi with $CO_2$. The reaction temperature rose from −45° C. to −42° C. over 3 minutes. The slurry was aged with vigorous stirring at −45° C. for 1 hour and assayed as above.

The dark brown mixture was warmed to 0° C. in an ice water bath, and 200 mL of 2N HCl was added over 3 minutes. The vigorous quench reaction was controlled by slow addition of the acid solution. The biphasic mixture was aged with vigorous stirring for 20 minutes. The layers were separated and the organic layer assayed (95.8 mol % acid). The aqueous layer was backwashed 1×200 mL with toluene. The combined organic layer was concentrated in vacuo at 32° C. (50–80 torr), collecting 280 mL of distillate. Toluene (175 mL) was added to bring the batch volume to 250 mL for assay (97 mol % acid) and further workup. Aqueous 5% $Na_2CO_3$ (200 mL) was added and the layers were separated. Any rag material was kept with the organic layer. Solka floc (2 g) was added to the aqueous layer (pH 9.5), and the resulting slurry was filtered through a 12 g pad of solka floc which had been prewashed with water. The cake was then washed with 100 mL of water.

The pH was adjusted to 5.9 with the addition of concentrated HCl (25 mL). The batch was treated with 100 mg of 3,5-bis(trifluoromethyl)benzoic acid as a seed and then aged at ambient temperature for 35 minutes, after which time a nice seedbed was observed. Concentrated HCl (15 mL) was added to adjust the pH to 1.9. The material was aged for 1 hour, at which time the supernatant assayed for 0.2 g/L. The flocculent white solid was filtered through a medium pore fritted funnel and washed (displacement) 2×100 mL with mother liquor and 1×100 mL with DI water. The material was dried for 0.5 hour in vacuo under a nitrogen cone. The material was then dried overnight at 35° C. in a vacuum oven under a $N_2$ sweep, to provide 24.12 g (99 wt %, 94% isolated yield) of the desired product as a white crystalline solid (KF=0.1 wt %).

| Column: | Inertsil ODS-3, 4.6 mm × 25 cm | |
|---|---|---|
| Eluent A: | MeCN | |
| Eluent B: | pH 6.5 phosphate buffer, 10 mM, 10% MeCN | |
| Gradient: | 0–4 min | 65% A |
| | 4–10 min | 65% A–90% A |
| | 10–15 min | 90% A |
| | 15–17 min | 90% A–65% A |
| | 17–20 min | 65% A |
| Injection: | 20 mL | |
| Flow rate: | 1.5 mL/min | |
| Detection: | 210 nm | |
| Temperature: | 35 ° C. | |
| Retention Times: | Bromide ion | 1.5 min |
| | 2,6-Carboxylic Acid | 1.8 min |
| | 2,5-Carboxylic Acid | 1.9 min |
| | 2,4-Carboxylic Acid | 1.9 min |
| | Desired 3,5-Carboxylic Acid | 2.2 min |
| | Toluene | 5.3 min |
| | 3,5-Bis(trifluoromethyl)benzene | 7.0 min |
| | 3,5-Bis(trifluoromethyl)bromobenzene | 9.5 min |
| | Ketone | 11.6 min |
| | Dimer | 12.6 min |
| | Carbinol | 13.3 min |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for the preparation of a compound of the formula:

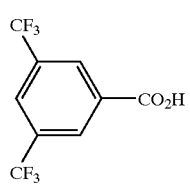

which comprises:

a) treating a Grignard reagent of the formula:

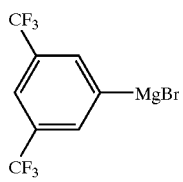

with carbon dioxide at a pressure of 1 to 40 psi in an organic solvent at an initial temperature of less than about −10° C., b) followed by treating the product therefrom with a strong acid to give the compound of the formula:

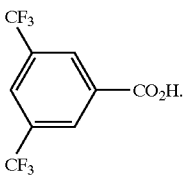

2. The process of claim 1 wherein the organic solvent is selected from: tetrahydrofuran, toluene, diethyl ether, diglyme, and methyl t-butyl ether.

3. The process of claim 1 wherein the organic solvent is tetrahydrofuran.

4. The process of claim 1 wherein the carbon dioxide gas is at a pressure of about 2 to 10 psi.

5. The process of claim 1 wherein the carbon dioxide gas is at a pressure of about 3 psi.

6. The process of claim 1 wherein the temperature of the reaction mixture upon addition of the carbon dioxide is less than about −20° C.

7. The process of claim 6 wherein the temperature of the reaction mixture upon addition of the carbon dioxide is less than about −40° C.

8. The process of claim 7 wherein the temperature of the reaction mixture upon addition of the carbon dioxide is less than about −45° C.

9. The process of claim 1 wherein the strong acid is selected from: hydrochloric acid, sulfuric acid, and methanesulfonic acid.

10. The process of claim 9 wherein the strong acid is hydrochloric acid.

* * * * *